United States Patent [19]

Swanson et al.

[11] Patent Number: 5,111,812
[45] Date of Patent: May 12, 1992

[54] DEFILBRILLATION ELECTRODE HAVING SMOOTH CURRENT DISTRIBUTION

[75] Inventors: David K. Swanson, Roseville; Roger W. Dahl, Andover; Douglas J. Lang, Arden Hills, all of Minn.

[73] Assignee: Cardiac Pacemakers, Inc., St. Paul, Minn.

[21] Appl. No.: 468,739

[22] Filed: Jan. 23, 1990

[51] Int. Cl.[5] .............................................. A61N 1/39
[52] U.S. Cl. .................................. 128/419 D; 128/784
[58] Field of Search ............... 128/419 D, 419 P, 786, 128/784

[56] References Cited

U.S. PATENT DOCUMENTS

| | | | |
|---|---|---|---|
| 2,985,172 | 8/1959 | Jones | 128/416 |
| 3,380,445 | 9/1965 | Frasier | 128/2.06 |
| 3,662,757 | 5/1972 | Blackett | 128/416 |
| 4,291,707 | 9/1981 | Heilman et al. | 128/784 |
| 4,548,203 | 10/1985 | Tacker, Jr. et al. | 128/419 D |
| 4,567,900 | 2/1986 | Moore | 128/784 |
| 4,641,656 | 2/1987 | Smits | 128/419 D |
| 4,708,145 | 11/1987 | Tacker, Jr. et al. | 128/419 DS |
| 4,711,251 | 12/1987 | Stokes | 128/784 |
| 4,736,752 | 4/1988 | Munck et al. | 128/798 |
| 4,774,952 | 10/1988 | Smits | 128/419 D |
| 4,807,621 | 2/1989 | Hagen et al. | 128/303.13 |
| 4,817,634 | 4/1989 | Holleman et al. | 128/784 |
| 4,860,769 | 8/1989 | Fogarty et al. | 128/786 |
| 4,865,037 | 9/1989 | Chin et al. | 128/419 |
| 4,951,668 | 8/1990 | Reed | 128/419 R |
| 4,969,463 | 11/1990 | Dahl et al. | 128/419 D |

FOREIGN PATENT DOCUMENTS 3530269 2/1987 Fed. Rep. of Germany .
2182566 5/1987 United Kingdom .

*Primary Examiner*—William E. Kamm
*Assistant Examiner*—Kennedy J. Schaetzle
*Attorney, Agent, or Firm*—Fleit, Jacobson, Cohn, Price, Holman & Stern

[57] ABSTRACT

A defibrillation electrode for implantation in the region of the heart and for connection to a defibrillation system. The electrode comprises multiple independent conductive segments spaced apart for defining a discharge surface of the electrode. In one embodiment, the electrode comprises a plurality of concentric conductive rings electrically connected together. To smooth the current distribution, the interface impedance of the inner conductive segments is made lower than that of the outer conductive segments. In one embodiment, the impedance is determined by the choice of the conductive material. In another embodiment, the impedance is determined by texturing the surface of the conductive segments. In yet another embodiment, the impedance is determined by the ratio of conductive edges to surface of the conductive segment. The discharge surface region can also take the form of a portion of a cardiac catheter.

Other ways to control the current distribution include the use of a floating conductive segment, and the use of discrete segments which receive defibrillating waveforms of different amplitudes and isolating the conductive segments to deliver higher amplitude waveforms in the inner segments than the outer segments.

10 Claims, 4 Drawing Sheets

DEFILBRILLATION ELECTRODE HAVING SMOOTH CURRENT DISTRIBUTION

BACKGROUND OF THE INVENTION

This invention relates to an electrode for medical applications, and more particularly to an implantable cardiac cardioversion/defibrillation electrode.

Electrodes implanted in the body for electrical cardioversion or defibrillation of the heart are well known. More specifically, electrodes implanted in or about the heart have been used to reverse (i.e., defibrillate or cardiovert) certain life-threatening cardiac arrhythmias, where electrical energy is applied to the heart via the electrodes to return the heart to normal sinus rhythm. See, for example, commonly assigned U.S. Pat. No. 4,291,707 to Heilman, relating to a planar patch defibrillation electrode, and pending U.S. patent application Ser. No. 07/334,652, entitled Cardiac Defibrillation/Cardioversion Spiral Patch Electrode, filed Apr. 10, 1989.

The Heilman patent specifically discloses an implantable cardiac electrode comprised of a planar conductive material insulated completely on one side and partially on its other side. Apertures are provided around the insulated perimeter of the partially insulated side of the electrode to provide for efficient and uniform energy transfer to the heart tissue by eliminating the so called "edge-effect".

The pending application Ser. No. 07/334,652 relates to a spiral patch electrode comprised of an elongated conductor preformed to adapt a spiral planar patch configuration when deployed on or about the heart surface.

The amount of energy delivered by the electrodes to the heart during defibrillation (or cardioversion) depends on the placement of the electrodes and the ability of the electrodes to distribute the energy uniformly throughout a major portion of the heart. This energy is called the defibrillation or cardioversion energy.

For purposes of the following discussion, no distinction will be made between cardioversion and defibrillation, although the respective energy levels and timing sequences may differ. Both will be referred to as defibrillation.

A problem with many defibrillation electrodes is that they fail to provide a uniform current discharge distribution. Specifically, high current densities occur near the edges or perimeter of the electrode which damages underlying tissue. In addition, the high current densities along the perimeter of the electrode result in a large potential drop near the electrode which greatly reduces the voltage gradient within the myocardial mass. Therefore, the effectiveness of the defibrillation pulse is hindered.

Some attempts have been made to obtain more uniform current distribution on externally applied electrodes for external pacing or defibrillation. One such device comprises an externally applied patch system for defibrillation which reduces the potential for skin burning during external defibrillation.

This approach involves the use of various resistances to force a greater percentage of total current towards the center of an externally applied electrode. However, in the field of implantable devices, the amount of energy available is finite. Consequently, implantable defibrillation electrodes must provide a uniform current distribution with minimal interface impedances.

SUMMARY OF THE INVENTION

The present invention relates to an electrode configuration and circuitry which minimizes the defibrillation energy by smoothing or focusing the discharged electric field so that the electrical energy uniformly and efficiently reaches and is applied across the heart. When electrical energy is applied between defibrillation electrodes, it has been recognized that the discharging of the energy favors the perimeter of the conductive portion of the electrodes. To smooth the current distribution, modifications are made to the conductive portions of the electrode to lower the interface impedance at the center of the electrode segments.

When using the term impedance hereinafter, it is understood that this is the impedance associated with the conversion of electronic current to ionic current, and is commonly referred to in the art as the interface impedance. In the concentric electrode configuration, the interface impedance at the center of the electrode is made lower relative to the interface impedance at the extremes to provide a uniform current distribution across the conductive surface of the electrode.

Interface impedance modifications are accomplished in one of several ways. First, the material composition of the conductive rings is varied so that a material having a higher activation energy is used for the extreme conductive segments than the material used for the inner segments. Second, the texture of the surface of select ones of the conductive segments is modified to vary the surface area.

Texturing can be effected in several ways. The surface features can be modified in a "macro"0 sense by knurling or scribing the surface, and in a "micro" sense by platinizing the conductive segment. Giving more texture to the conductive segment increases the surface area, thus, decreasing interface impedance of the conductive segments. Alternatively, the segments are constructed of conductive screens formed of woven filaments. The spacing between and diameter of the filaments can be modified to alter the surface area of the segment to change its interface impedance. Yet another way to vary the texture is to vary the ratio of conductive filament edge to the surface area of the conductive segment.

Another impedance compensation technique is to use multiple layers of conductive screen for select ones of the segments. A multiple screen layer has a larger surface area, thus reducing the interface impedance of the segment.

Further, the dimensions of each conductive segment can be modified to compensate for impedance irregularities across the electrode. The central segments are made wider than the extreme segments so that the interface impedance is reduced at the center. This can be applied to both patch and catheter electrodes.

In another embodiment, the impedance irregularities are compensated for electrically by applying different voltage levels to the conductive segments. The conductive segments are all electrically isolated from each other and connected to a distinct conductor in an electrode lead which conveys the voltage waveforms to the segments from the defibrillation electronics.

In yet another embodiment, all but a select one (or ones) of the conductive segments are connected in common. The lone segment (or segments) is isolated from the applied voltage and is designed to act as a floating electrode when electrical energy is applied to the electrically active conductive segments. Voltage is induced on the floating electrode from the active segments to effect a uniform distribution across the electrode discharge surface.

The primary purpose of the present invention is to provide a variety of ways to control the current distribution across the surface of an electrode. The techniques described hereinafter to do this may be employed to develop a uniform current distribution or to focus (or direct) the defibrillation energy. The latter utility includes the formation of various irregular current distributions at the interface of a particular electrode that may be used to insure that a uniform voltage gradient is developed within the heart Furthermore, the principles and advantages described hereinafter are applicable on patch electrodes on or about the heart, endocardial catheter electrodes, and subcutaneous electrodes. The terminology "in the region of the heart" is hereinafter meant to include physically in contact with the heart, within the pericardial space, beneath the skin and outside the pericardial space (subcutaneous), and inside the heart (as, for example, with an endocardial catheter electrode).

DETAILED DESCRIPTION OF THE DRAWINGS

Figure 1A:
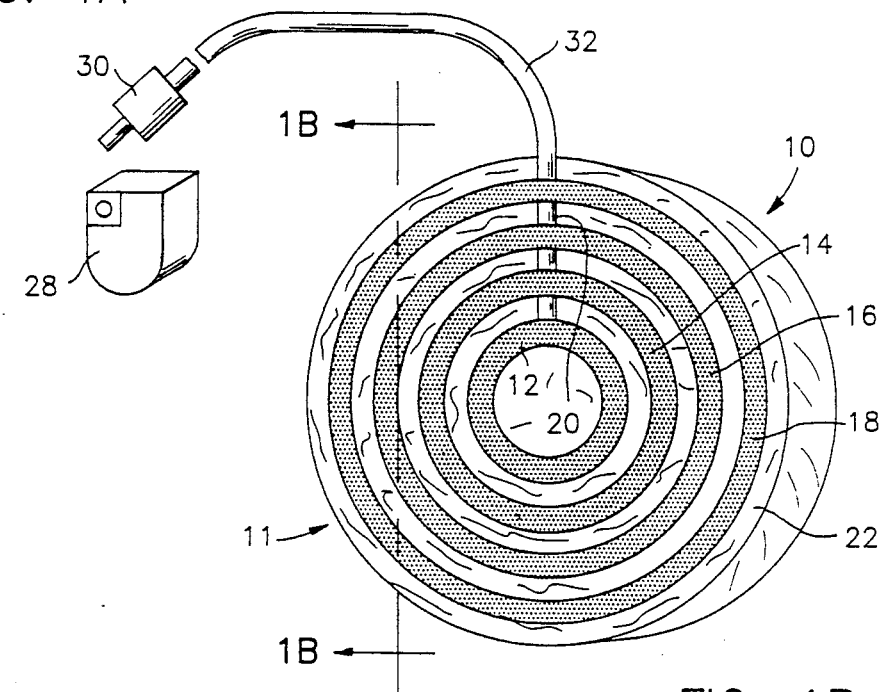
FIG. 1A is a perspective view of the discharge surface of the defibrillation electrode comprising the first embodiment of the present invention.
Figure 1B:
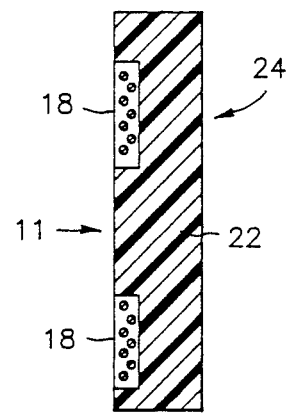
FIG. 1B is a cross-sectional view taken through line 1B—1B of FIG. 1A.

Referring first to FIGS. 1A and 1B, a defibrillation electrode of the first embodiment of the present invention is shown at 10. Electrode 10 is a patch electrode for implantation in the region of the heart. Electrode 10 is shown as a circular element having a substantially planar discharge surface region 11 comprising spaced concentric conductive rings 12, 14, 16, and 18. The conductive rings are connected to each other by conductor 20.

Insulation 22 covers the entire back surface 24 opposite the discharge surface region 11, and occupies the area defined by the concentric rings of the electrode. The discharge surface region 11 is a planar or flat surface, and the conductive rings are embedded on the insulation 22. In a modified form electrode 10 may be constructed without insulation 22.

While the electrode 10 is shown in a concentric ring configuration, it is considered within the scope of this invention to form a defibrillation electrode of a construction similar to that shown in FIG. 1, but in various other configurations and geometrical shapes. Furthermore, while the type of conductive and insulative material used to form defibrillation electrodes varies, it is envisioned that electrically conductive materials such as titanium mesh are used in constructing the electrode 10. In addition, although the size and dimension of the electrode can be altered, the overall conductive surface area of the electrode 10 is on the order of 10–100 sq. cm.

In use, electrode 10 is implanted in the region of the heart, together with at least one other implanted electrode of similar or other type of construction and connected to an implanted cardioverter/defibrillator 28 by plug 30 at the end of insulated lead 32 electrically connected to the electrode as shown in FIG. 1. The lead 32 includes an electrically conductive wire that extends through the back surface 35 of the electrode and connects to at least one of the conductive surfaces.

It has been found that electrical discharge favors the perimeter of the electrode where the interface impedance is lower than at the center of the electrode. Thus, lowering the interface impedance at the center of the electrode relative to the interface impedance at the extremes, smooths the current distribution across the discharge surface.

One way to accomplish this is to vary the material composition comprising each of the conductive rings. A material with a low activation energy, such as platinum, is used for the central conductive rings 12 and 14, while a material with a higher activation energy, such as titanium, is used for the outer rings 16 and 18. The conductive material is chosen so that the interface impedance increases gradually from the center of the electrode 10 to the periphery.

Another way to vary the impedance is to alter the texture of the surface of the conductive rings. By giving a particular ring more texture, the surface area of the ring is increased, thus reducing the interface impedance of the ring. Using this method, the outer conductive rings would be kept smooth while the inner rings would be roughened. The inner rings 12 and 14 would be substantially textured while gradually moving outward, the outer rings would be less textured. The rings can be textured in a "macro" sense by knurling or scribing the surface to create surface changes visible to the naked eye, or in a "micro" sense by platinizing the surface to decrease the interface impedance. Platinizing is the process by which fine platinum particles are coated on the surface of the conductive segment. Such surface changes are not visible to the naked eye.

Figure 2:
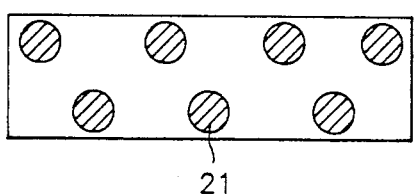
FIGS. 2 and 3 are partial cross-sectional views of a single conductive segment of the electrode shown in FIG. 1
Figure 3:
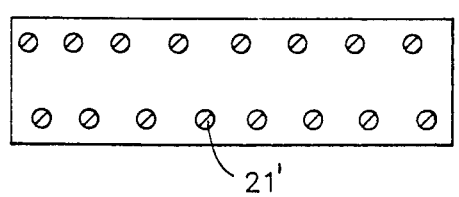

Yet another way to vary the texture and hence the interface impedance is to change the filament dimensions and spacings in a conductive screen comprising a conductive ring. FIGS. 2 and 3 illustrate a cross-section of a single conductive ring having different sized filaments and spacings. These conductive rings are formed of woven conductive filaments 21, to form a mesh screen. In FIG. 2, the conductive filaments 21 are larger in diameter and spaced closer together than the filaments 21' in FIG. 3. Thus, in a ring formed of a conductive screen, the ring in FIG. 1 has more reactive surface area than that of FIG. 2. However, the filaments 21' of the ring in FIG. 3 are finer and hence have better fatigue characteristics. Thus, the surface areas of a ring can be increased, but at the expense of the fatigue characteristics of the screen. By choosing a particular filament diameter and spacing the surface area of the screen, the interface impedance can be controlled.

Figure 4:
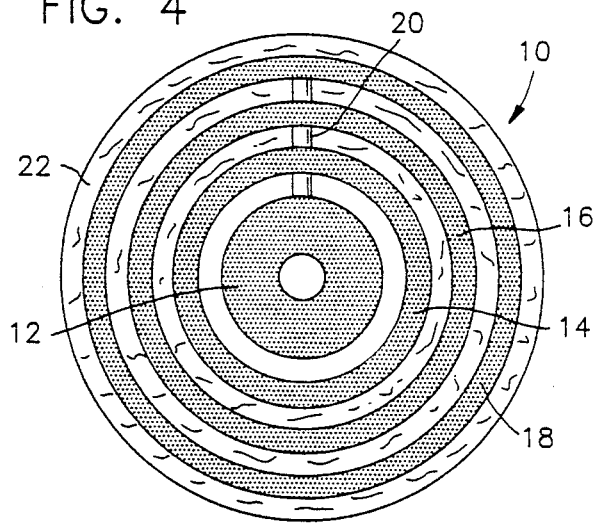
FIG. 4 is a plan view of the discharge surface region of a modified version of the electrode illustrated in FIG. 1.

Increasing the conductive edge to surface area ratio decreases the interface impedance while decreasing the edge to surface area ratio increases the interface impedance. In addition, as shown in FIG. 4, by making the inner conductive rings 12 and 14 wider than the outer conductive rings 16 and 18, and making the variation a continuum moving from the center of the electrode to the perimeter, then the interface impedance at the center of the electrode will be lowest and will gradually increase moving outward so that the discharge will be uniform across the electrode.

Another way to vary the interface impedance is to provide a multiple layer of conductive screens for select ones of the conductive rings. A multiple layer screen has an increased surface area which effectively reduces the interface impedance.

Figure 5:
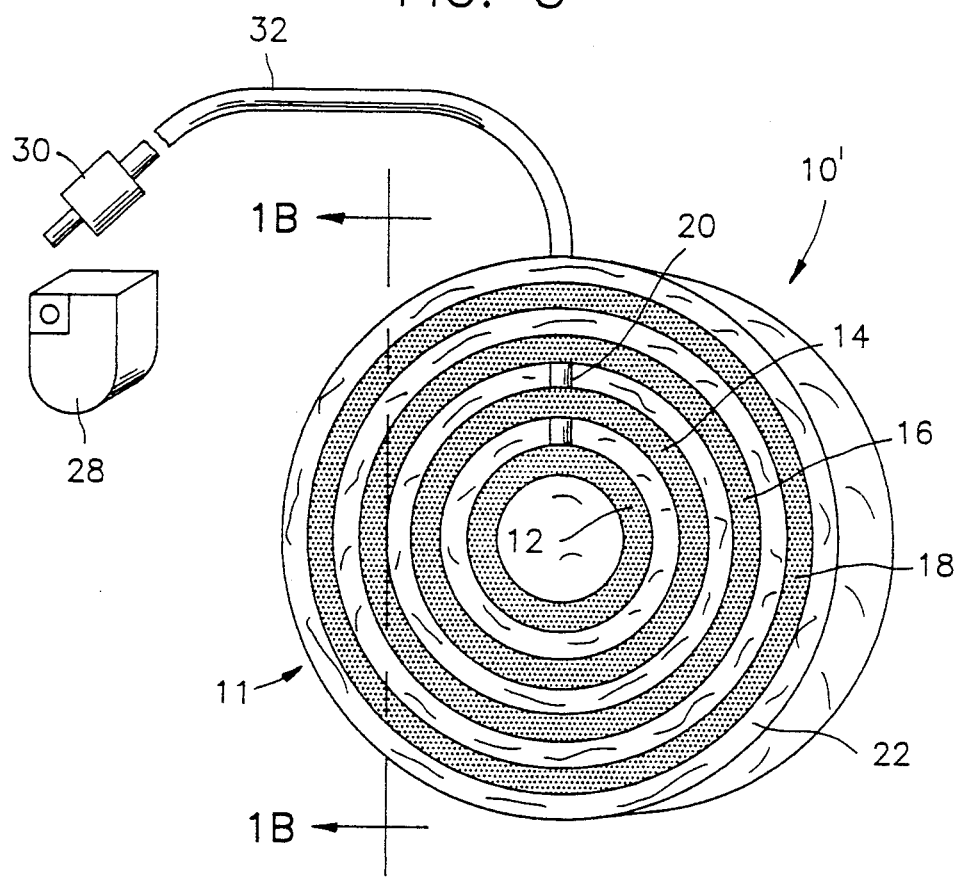
FIG. 5 is a perspective view of the discharge surface of the defibrillation electrode comprising the second embodiment of the present invention.

FIG. 5 illustrates the defibrillation electrode of the second embodiment. Electrode 10' is similar to electrode 10 except that the conductive ring 18 is not electrically connected to the other conductive rings or to the pulse generator 28. The conductive ring 18, in this embodiment, is a floating conductive segment. Because the conductive rings 12, 14, and 16 are connected together and to the pulse generator 28, these conductive rings are active electrode segments. The active electrode segments (rings 12-16) impose a voltage on the floating segment 18 in the electric field applied thereto. The floating segment 18 serves to control and smooth the current distribution across the electrode surface. Electrical connections from the lead 32 are made at the center of the electrode 10'. While only one floating segment is shown, there may be more than one. The floating and active segments can be interlaced. The separation between the active and floating segments insures relatively high current densities at the center of the electrode to create a uniform discharge.

Figure 6:
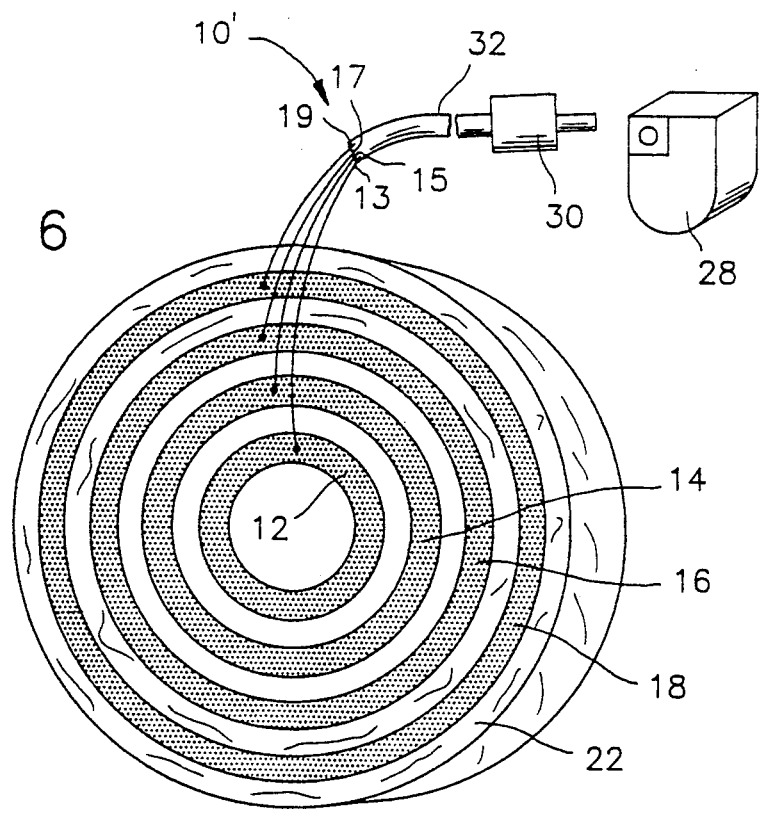
FIG. 6 is a perspective view similar to FIG. 1 and illustrating a third embodiment of the present invention.

FIG. 6 illustrates electrode 10" of the third embodiment of the present invention. As described previously, during discharge, the interface impedance at the center of the electrode is generally higher than at the extremes. The current density is greatest at the periphery when the same voltage is applied to the entire electrode. Electrode 10" compensates for this by having each conductive ring isolated from each other to receive a distinct voltage simultaneously. Specifically, the lead 32 conveys, via four conductors 13, 15, 17, and 19, four voltages to the conductive segments 12, 14, 16, and 18, respectively, of electrode 10'. The inner most rings would receive higher voltages than the outer rings, and the variation therebetween is a continuum moving outward. By this, the interface impedance effects are electrically compensated for to deliver a uniformly distributed current discharge to the heart.

Having found that highly efficient discharges are possible, electrodes 10' and 10", in a modified form, may be constructed without the insulation backing 22.

Figure 7:
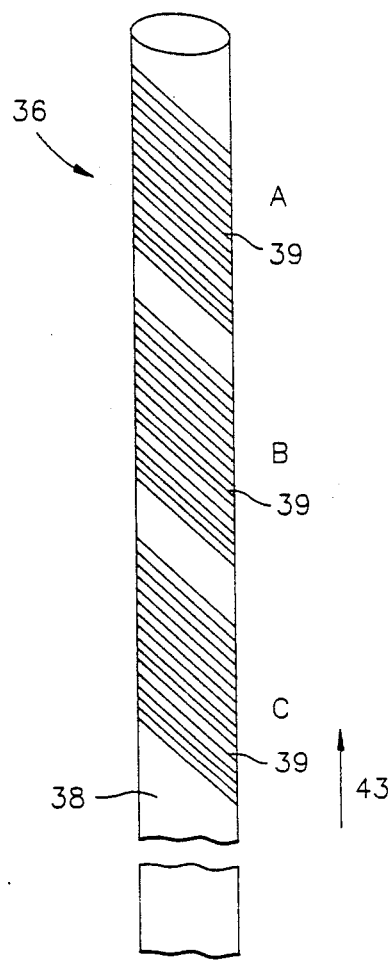
FIG. 7 is a perspective view of the active portion of a endocardial catheter defibrillation electrode comprising the fourth embodiment of the present invention.

FIG. 7 illustrates an endocardial catheter electrode 36 of the fourth embodiment. Electrode 36 is designed for implantation in the heart via one of the great veins leading to the heart, such as, for example, the superior vena cava. The electrode 36 comprises a cardiac catheter 38 having a series of three discrete conductive segments A, B, and C on the distal active portion 43 of the catheter 36. Each conductive segment comprises a coil of platinum coated titanium ribbon 39, or the like, wrapped around the catheter 38

The conductive segments A, B and C are modified so that the interface impedance of segment B is made lower than A and C, while all the segments receive the same voltage to discharge. Similar to electrode 10, this can be done by using a material with a higher activation energy for segments A and C, and a material with a lower actuation energy for segment B. Alternatively, to change the surface area of segment B the dimensions of the ribbon 39 can be reduced to use two ribbons in place of one wound around the catheter. Thus the segment would have a higher edge to surface area ratio and a lower interface impedance. Additionally, the pitch of the ribbon 39 or spacing between adjacent turns of the ribbon 39 can be varied to change the surface area, and hence the interface impedance of the conductive segment. Further, the texturing techniques described in conjunction with the patch electrode 10 can also be applied to the conductive segments of the endocardial catheter 36.

Figure 8:
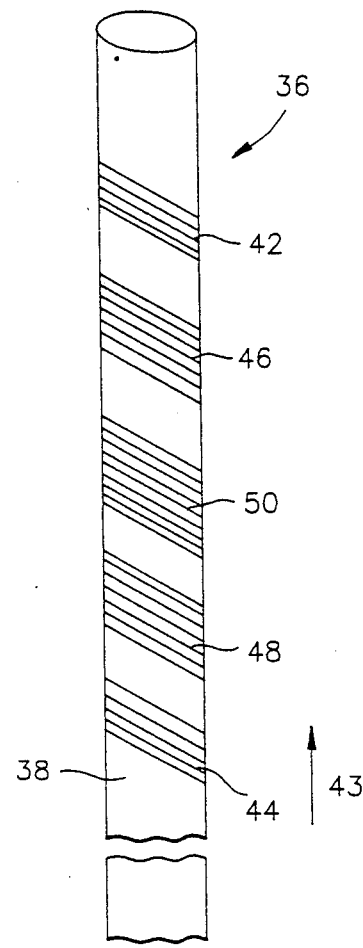
FIG. 8 is a perspective view similar to FIG. 7 and illustrating a modified version of the endocardial catheter electrode of the fourth embodiment.

FIG. 8 illustrates a modification to electrode 36 similar to that illustrated in FIG. 4. Instead of three segments, five segments are shown on the catheter 38. The extreme segments 42 and 44 are considerably narrower than segments 46 and 48. Segment 50 is the widest of all the segments. By this arrangement, the interface impedance at the central, or mid length portion of the catheter is decreased relative to the extreme portions. As such, a more uniform discharge can be delivered.

The endocardial catheter electrode 36 can also employ the floating electrode principle by connecting segment B to a source of defibrillation energy while leaving segments A and C floating. During discharge, a voltage is imposed on segments A and C from segment B to control and effect a uniform distribution across the electrode. To improve the efficiency of the floating segments A and C, they may be interlaced with additional active segments.

In yet another form similar to electrode 10" separate conductors (not shown) run the length of the catheter 36 and connect to distinct conductive segments on the electrode to deliver distinct voltage waveforms thereto. The inner segment B would receive a higher voltage than the outer segments A and C to effect a uniform discharge.

Figure 9:
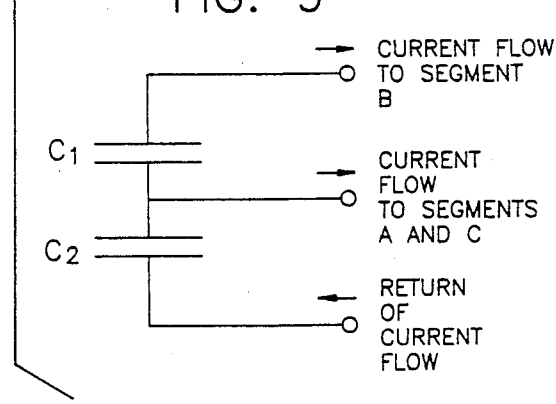
FIGS. 9 and 10 are schematic diagrams of capacitor circuits for developing a plurality of discharge voltages in accordance with the third embodiment of the present invention.
Figure 10:
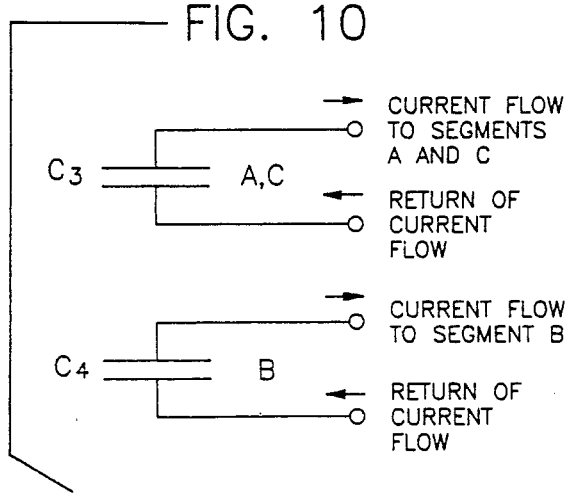

To generate multiple amplitude voltages, either a series or parallel capacitor configuration is used, as illustrated in FIGS. 9 and 10. For the three segment electrodes illustrated in FIG. 7, segments A and C are connected together as the common voltage while segment B is the higher voltage. In FIG. 9, a series connection of capacitors C1 and C2 is shown whereby segment B receives the voltage across capacitors C1 and C2 and segments A and C receive the voltage across capacitor C2. In FIG. 10, segments A and C receive the voltage across the capacitor C3 and segment B receives the higher voltage across capacitor C4. In either case, the current flow is as shown in the Figures by the arrows to the segments so that the current distribution across the discharge region 43 is uniform.

Figure 11:
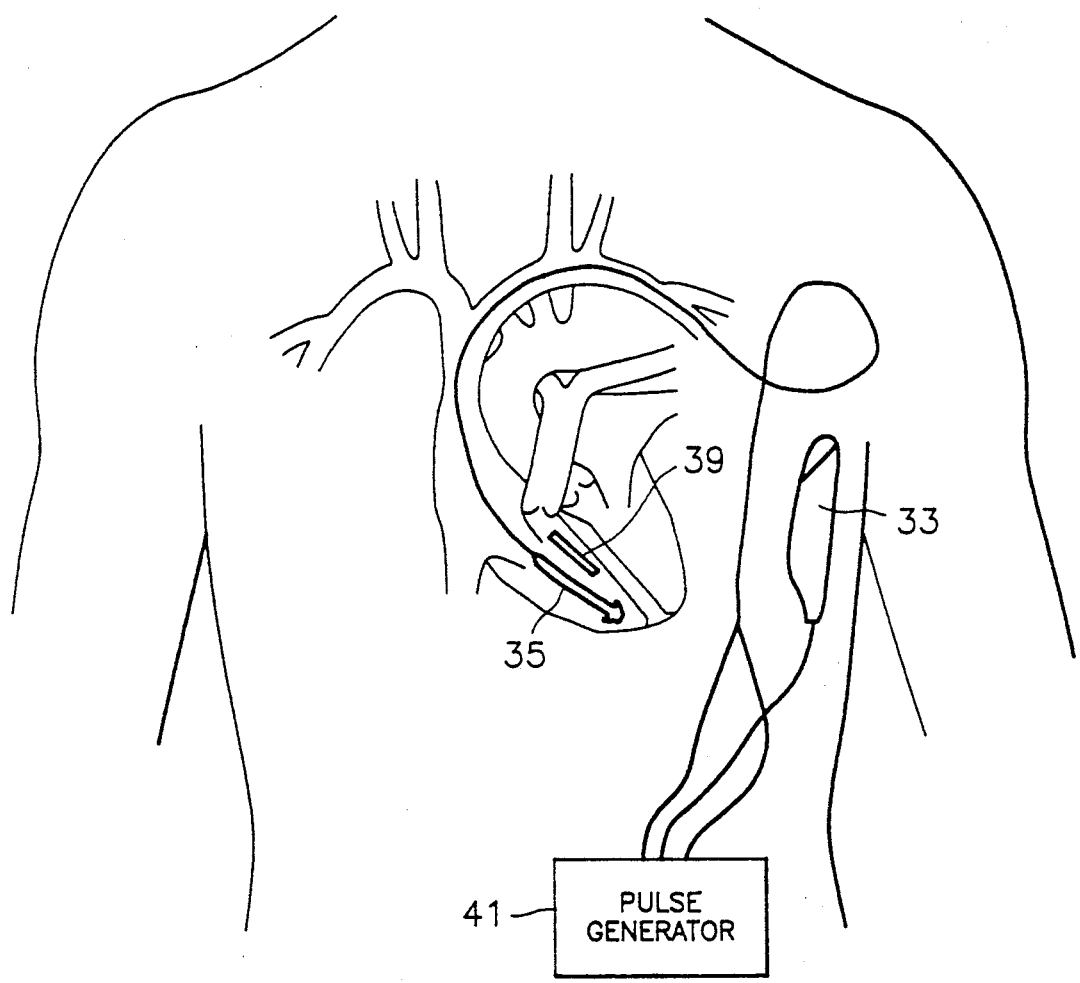
FIG. 11 is a schematic diagram illustrating a deployable floating electrode used in a defibrillation system.

Finally, the concept of a floating electrode is also adaptable as a separate deployable electrode as schematically shown in FIG. 11. Electrodes 33 and 35 are the active electrodes to be discharged against each other from the pulse generator 41. In addition, a floating electrode 39 is positioned inside the heart and fixed to the wall of the right ventricle. During discharge, the active electrodes 33 and 35 impose a voltage on the floating electrode 39 for effecting a uniform discharge across the heart for defibrillation. Alternatively, a patch electrode may be employed to serve as the floating electrode.

The techniques described above for controlling the discharge of a defibrillation can be used in at least two ways. First, and as clearly described above, the generation and delivery of a uniform discharge can be accomplished. Second, and though not discussed above thoroughly, the same techniques for effecting uniform discharge or smooth current densities can also be employed to focus and create irregular distributions at the interface of a particular electrode to create a desired overall distribution in the heart, or to focus energy to a particular area of the heart.

The above description is intended by way of example only and not intended to limit the present invention in any way except as set forth in the following claims.

We claim:

1. An implantable defibrillation/cardioversion system including at least two defibrillation electrodes implanted in the region of the heart, said system comprising:
    an implantable defibrillation electrode comprising a conductive discharge surface region having a predetermined surface area for delivering electrical energy to the heart, said discharge surface region comprising multiple discrete conductive segments;
    pulse generating means including means for generating multiple simultaneous shock pulses of differing voltages which multiple shock pulses are discharged simultaneously and thereby define a single defibrillation/cardioversion shock; and
    lead means including a plurality of conductors, each of said conductors connected to select ones of said conductive segments and to said pulse generating means for conveying select ones of said shock pulses to said select ones of said conductive segments.

2. The system of claim 1 wherein said conductive segments are concentrically spaced conductive rings.

3. The system of claim 1 wherein said discharge surface region is defined by a surface portion of a predetermined length of a catheter.

4. The system of claim 1, wherein said lead means connects between said pulse generating means and the conductive segments of said electrode so that the conductive segments at the center of said discharge surface region receive higher voltage shock pulses than conductive segments at the extremes of said discharge surface region.

5. The system of claim 1, wherein said pulse generating means comprises a series connection of a plurality of capacitors, the voltage across various combinations of said capacitors corresponds to one of said differing voltages.

6. The system of claim 1, wherein said pulse generating means comprises a parallel connection of a plurality of capacitors, the voltage across each capacitor corresponding to one of said differing voltages.

7. An implantable defibrillation/cardioversion system including at least two defibrillation electrodes implanted in the region of the heart, said system including:
    an implantable defibrillation electrode comprising an elongated catheter having a distal active region and a proximal lead region, multiple independent conductive segments spaced apart and positioned along the length of said elongated catheter;
    pulse generating means including means for generating multiple simultaneous shock pulses of differing voltages which multiple shock pulses are discharged simultaneously and thereby define a single defibrillation/cardioversion shock; and
    lead means including a plurality of conductors, each of said conductors connected to select ones of said conductive segments and to said pulse generating means for conveying select ones of said shock pulses to said select ones of said conductive segments.

8. The system of claim 7, wherein the lead means connects to said pulse generating means and the conductive segments of the electrode so that the conductive segments at the extremes of said distal active region receive lower voltage shock pulses than the conductive segments at the mid-length portion of said distal active region.

9. The system of claim 7, wherein said pulse generating means comprises a series connection of a plurality of capacitors, the voltage across various combinations of said capacitors corresponds to one of said differing voltages.

10. The system of claim 7, wherein said pulse generating means comprises a parallel connection of a plurality of capacitors, the voltage across each capacitor corresponding to one of said differing voltages.

* * * * *